United States Patent [19]

Sørensen et al.

[11] 4,231,369

[45] Nov. 4, 1980

[54] SEALING MATERIAL FOR OSTOMY DEVICES

[75] Inventors: Erik L. Sørensen, Helsinge; Hans-Ole Larsen, Farum, both of Denmark

[73] Assignee: Coloplast International A/S, Espergaerde, Denmark

[21] Appl. No.: 906,549

[22] Filed: May 17, 1978

[30] Foreign Application Priority Data

May 24, 1977 [GB] United Kingdom ............... 21767/77

[51] Int. Cl.$^3$ ............................................... A61F 5/44
[52] U.S. Cl. ..................................................... 128/283
[58] Field of Search ........................................ 128/283

[56] References Cited

U.S. PATENT DOCUMENTS

| 2,908,658 | 9/1975 | Marsan | 128/283 |
| 3,339,546 | 9/1967 | Chen | 128/156 |
| 3,612,053 | 10/1971 | Pratt | 128/283 |

FOREIGN PATENT DOCUMENTS

| 290223 | 3/1966 | Australia . |
| 576665 | 4/1946 | United Kingdom . |
| 960880 | 6/1964 | United Kingdom . |
| 981372 | 1/1965 | United Kingdom . |
| 1088992 | 10/1967 | United Kingdom . |

OTHER PUBLICATIONS

Kutscher et al., "A New Vehicle (Orobase) for the Application of Drugs to Oral Membranes," *Oral Surg. Oral Path*, vol. 12, pp. 1080–1089, (1959).

*Adhesion in Biological Systems*, Chap. 10, Chen et al., 1970.
*J. Am. Pharm. Assoc. Sci. Ed.*, vol. 45, pp. 212–218, Mutimer et al.
*Aspects of Adhesion*, vol. 1, pp. 81–89, Salter, "The Testing of Adhesives Used with Decorative Laminates."
*J. Am. Dental Assoc.*, vol. 35, pp. 644–647, Scrivener, "Penicillin: New Methods for its Use in Dentistry."
"Adhesives", pp. 194–195, 586–587, Skeist.
"Polyethers", pp. 273–274, Gaylord, (1964).
"The Technology of Plastics & Resins", pp. 284–285, Mason et al., (1945).
"Adhesives in the Paper Industry", pp. 22, Dyck, (1960).
"Technology of Adhesives", pp. 162–165, Delmonte, (1947).

*Primary Examiner*—C. Fred Rosenbaum
*Attorney, Agent, or Firm*—Lawrence Rosen; E. Janet Berry

[57] ABSTRACT

The invention relates to a sealing material for use in connection with ostomy devices, particularly stoma pouches, to surround and protect a stoma in the human body. The improvement is that the material is a shaped, gel-like composition composed of a largely continuous phase consisting of a physically cross-linked elastomer or a mixture of such elastomers, and preferably, but optionally, one or more hydrocarbon tackifier resins and likewise optionally, but preferably, an oil extender; and distributed in the continuous phase one or more hydrocolloids. The gel-like composition has a low resistance to quick deformation and a rapid recovery to the original shape after deformation.

22 Claims, 1 Drawing Figure

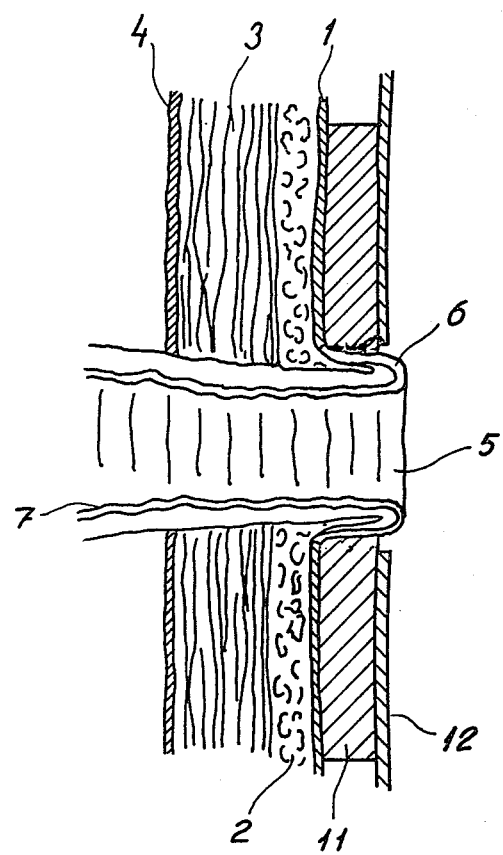

SEALING MATERIAL FOR OSTOMY DEVICES

FIELD OF THE INVENTION

This invention relates to an improved seal and sealing material, preferably having adhesive properties, for ostomy devices, i.e. for devices such as for instance pouches for closing an artificial intestine opening in the body of a patient who has had a surgical operation such as colostomy, ileostomy ureterostomy or the like. The seal and sealing material may also be useful for apparatus for controlling anal incontinence.

BACKGROUND OF THE INVENTION

In surgery as mentioned there is provided a channel to the outer world through the body wall, a so-called stoma, through which faecal material, liquid, urine and/or gases are excreted. As it is not possible to control at will the excretion through such artificial stoma, it must be closed in some manner. It is often done by affixing a pouch or bag to collect the waste material excreted. The affixing of such pouch may be done by the aid of some adhesive which provides, at the same time, a seal between the body and the pouch ensuring that the waste material is not leaking out of the pouch.

To illustrate the anatomy of an artificial body opening of the kind referred to, and the position of a collecting pouch and a sealing gasket, reference is made to the drawing, showing schematically in section an artificial intestinal opening—the stoma—in the torso of a patient, together with a section of a sealing gasket and part of collecting pouch.

In the drawing, 1 is the epidermis, 2 corium and subcutis and 3 a layer of abdominal muscles. This is delimited from inner cavities of the body by mucous membranes and the like, such as peritoneum 4. An intestine 5 by a surgical operation has been led through the various tissues of the abdominal wall so as to form a stoma 6. It should be noted how stoma 6 is caused to protrude from the abdominal wall; this protrusion may be smaller and larger and is not always as long (perpendicularly to the abdominal wall) as shown in the drawing. The inner wall of the intestine 5 is covered by a mucous membrane 7 and it should be noted how mucous membrane 7 covers even the protruding part of the stoma and is pulled back and sutured to the epidermis so that the entire protruding stoma is covered with the intestinal mucous membrane. This mucous membrane is resistant to the intestinal fluids which are very agressive to normal skin (epidermis) and whereas the intestinal fluids do no harm to the intestinal mucous membrane, it is important to prevent them from coming into contact with epidermis 1.

The drawing also schematically shows part of a stoma pouch 12, normally of some plastic material such as polyethylene, to collect excretions from the intestine 5; as the pouch as such does not form any part of the present invention, only a part of its panel facing the abdomen is shown. The pouch may be replaced by some other closing means such as a plug. To provide a tight seal between the pouch and the abdominal wall, and also to protect the part of the epidermis surrounding the stoma, there may be provided a sealing gasket or washer 11 between the pouch 12 (or other closing means) and the abdominal wall. The present invention is concerned with material for the sealing washer or gasket 11. Provided it is properly made and affixed to the pouch, it will ensure that the intestinal waste is discharged into the pouch 12 with a minimum contact with the epidermis. However, in practice heretofore such contact is never completely avoided and skin-irritation caused by intestinal fluids is a constant burden on a large number of patients. It is a main object of the present invention to provide an improved sealing material for gasket or washer 11 which will ensure that the intestinal fluids do not come into contact with the epidermis (skin) of the patient.

Whereas it is widely recognized that a need exists for making a seal between the stoma device and the patient's torso in order to prevent the intestinal material collected in the stoma device from leaking out into the open, it has apparently not been realized that a second, and for the patient equally important, seal is required to prevent the intestinal material from coming into contact with the patient's skin. This applies both when the stoma is closed by a stoma pouch and when it is closed by a plug or similar device since in such cases there may well be a risk that intestinal fluids leak between the plug and parts of the body facing the plug.

PRIOR ART

Known sealing materials which may be used for ostomy devices are for example those described in U.S. Pat. No. 3,339,546 to Chen for the purpose of adhering to moist surfaces, especially for use in the oral cavity. Chen claims a bandage comprising a water impervious film having secured to one surface thereof an adhesive gum-like bonding composition comprising a blend of a water soluble or swellable hydrocolloid admixed with a water-insoluble viscous gum-like elastic binder. The hydrocolloid ensures that the composition will adhere to and remain in contact with the moist surface whereas the viscous gum-like binder provides dry tack and coherence. The only gum-like elastic binder exemplified is polyisobutylene but the patent also claims the use as elastic binder of natural rubber, silicone rubber, acrylonitrile rubber, polyurethane rubber, or sucrose acetate isobutyrate. It should be noted that although the patent specification uses the word "elastic" the properties desired—as far as one can assess from the exemplification by polyisobutylene and sucrose acetate isobutyrate—are not "elastic" in the normal sense of this word; the compositions disclosed rather have the properties of highly viscous liquids. The patent further describes the addition to the composition of a small amount of a plasticizer or solvent such as mineral oil or petrolatum. This improves the adherence characteristics or contributes to provide the desired consistency.

The sealing material disclosed by Chen in U.S. Pat. No. 3,339,546 has been found to be a plastic material with no elasticity, being hard and requiring significant forces to be deformed.

The material has a very low elongation at break and will not return to its original shape after deformation. Since it is highly viscous it will not follow the body movements and when the material is used for ostomy devices this will inevitably lead to leakage.

Marsan in U.S. Pat. No. 3,908,658 describes and claims a seal and appliance for ostomy patients wherein a sealing means for adhering to the patient's skin around the stoma is water-insoluble and composed essentially of a pressure sensitive adhesion gel body having uniform surface and internal properties of tack, cohesive strength providing elasticity, flexibility, and compressibility and manual kneadability, said gel consisting essentially of a mixture of mineral oil, styrene-isobutylene copolymer and ethylenevinyl acetate copolymer. According to some of the claims the ethylenevinyl acetate copolymer may be replaced by some other vinyl polymer which is compatible with the mineral oil (or some other oleaginous liquid) and which gels that liquid to a tacky pliable pressure sensitive mass.

The Marsan composition in U.S. Pat. No. 3,908,658 does not typically contain hydrocolloids or similar substances but he says that there can be added hydrophilic agents such as pregelatinized starch. The purpose of this seems merely to be to provide a predetermined controlled rate or degree or solubility of the hydrophilic components; this can be desirable, for example, for releasing medicinal materials or the like from the seal into the area of the stoma.

In practice it has been found that the compositions proposed by Marsan in U.S. Pat. No. 3,908,658 although having higher elongation at break have substantially the same drawbacks as the materials of Chen described above and in U.S. Pat. No. 3,339,546.

OBJECT OF THE INVENTION

As mentioned it is the object of the invention to provide a sealing material which will give a reliable seal between the ostomy device and skin (epidermis) of the human body, as well as a seal between the stoma and that portion of the epidermis which might otherwise be exposed to discharge from the intestine. It is a further object to provide a sealing material which is capable of maintaining both seals even during rapid body movement. A still further object is to provide a sealing material as mentioned which may further have adhesive properties.

More specifically, it is part of the object of the invention to relieve the drawbacks of the known sealing materials and provide a seal and sealing material which will solve the two sealing problems associated with stomas:—To get a good seal between the stoma device and the body to prevent leakage into the open, and to get a good seal between the stoma itself and the patient's skin to prevent contact with the intestinal fluids and the skin.

BRIEF DESCRIPTION OF THE INVENTION

In ostomy systems for covering intestinal and similar stomas in the human body, which ostomy systems comprise an ostomy device surrounding or covering the stoma and being attached to the human body by sealing means, the said objects are achieved if in accordance with the invention there is used as said sealing means a sealing material in the form of a shaped, gel-like composition comprising one or more physically cross-linked elastomers forming a continuous phase and one or more hydrocolloids dispersed therein, said composition having a low resistance to quick deformation and a rapid recovery to its original shape after deformation. Hereby the seal between the ostomy device and the epidermis of the human body as well as the seal between the stoma and that portion of the epidermis, which might be exposed to discharge from the stoma, are maintained even under rapid body movements.

By the expression "physically cross-linked elastomer" it is meant that the cross-links in the elastomer, which is of course a polymer, are not of a chemical (covalent) nature but of a physical nature, meaning that there are areas within the elastomer having a high crystallinity or areas having a high glass transition temperature.

It has been found very important when making a seal which should solve the two sealing problems in connection with a stoma that the sealing material is very soft and yet has proper elastic properties. Frequently the sealing material according to the invention will be polygonal to circular with a central, substantially circular opening substantially fitting the outer perimeter of a protruding stoma in a patient's body, and especially the sealing means my be ring-shaped or rectangular to square, yet with rounded corners and with a central opening, and adapted to be placed around a stoma protruding somewhat from the torso of the patient. With the seal according to the invention the user will be able to widen the ring and place it around the protruding stoma after which the ring returns quickly to its original shape and size and fits closely to the stoma to make the seal between the stoma and the skin, yet the material has a low modulus of elasticity so the seal will not cause any discomfort or disturb the blood circulation in the protruding stoma or elsewhere.

From the above it will be understood that the sealing material is elastic but in a special way. It is deformable by the influence of weak and rapid forces and will rapidly revert to the original shape, in other words it has a low modulus of elasticity and high elongation. It has virtually no flow and has a low permanent set.

The sealing material may further according to the invention possess adhesive properties which will assure a tight seal between the skin and the ostomy device, thus solving the second sealing problem in connection with stomas, i.e. that of leaking material and such leaking material coming into contact with the patient's skin (epidermis). The adhesive properties may be varied in formulation to suit a particular use, for instance to give a very strong adhesion when the weight of a heavy ostomy device should be carried by the seal.

As will be described more fully hereinafter, the gel-like composition may according to the invention contain one or more hydrocarbon tackifier resins forming part of the continuous phase; hereby the adhesive properties of the material may be increased.

Furthermore, the gel-like composition may according to the invention contain one or more oil extenders evenly distributed and forming part of the continuous phase.

To improve the keeping qualities of the gel-like composition it may according to the invention further contain a conventional antioxidant.

DETAILED DESCRIPTION OF THE VARIOUS EMBODIMENTS OF THE INVENTION

In the gel-like composition according to the invention the adhesion to a more or less moist body surface is increased by the use of a hydrocolloid or a mixture of hydrocolloids distributed as particles in the continuous ("rubber-like") phase of the gel-like composition. It will be understood that the mechanical properties which have been found to be required for a proper function as described above are retained in a "rubber-like" composition having a hydrocolloid dispersed therein.

In the broadest sense the gel-like composition according to the invention thus comprises a physically cross-linked elastomer and a hydrocolloid dispersed therein, said composition having a low resistance to quick deformation and rapid recovery to its original shape.

In the preferred embodiments the gel-like composition further comprises a tackifier resin forming part of the continuous phase, and in a still more preferred embodiment an oil extender selected from the group consisting of paraffin oil, polybutene and vegetable oil is also evenly distributed in the continuous phase and forming part thereof.

As preferred elastomers according to the invention can be mentioned styrene-olefin-styrene block copolymers. They are A-B-A blockcopolymers with polystyrene end blocks and a polyolefin rubber midblock. The polystyrene end blocks are thermodynamically incompatible with the rubber midblocks. Consequently there is phase separation in the solid state. The polystyrene in the styrene-olefin-styrene block polymers is about one third of the total molecule. Being the minor component, the hard polystyrene phase regions or domains are the discontinuous phase distributed throughout a rubber matrix.

The hard regions or domains form strong crosslinks which bond each end of each molecule into a network similar to that of conventionally vulcanized rubber. However the crosslinks can be temporarily released by heating or dissolving the network.

Because their high cohesive strength results from the physical crosslinks due to the polystyrene domains, rather than from a chemical crosslink as in vulcanized materials, the styrene-olefin-styrene rubbers offer advantages in ease and versatility in processing and application. Compared to conventional rubbers, they have very low molecular weights.

These block copolymer molecules are linear with molecular weights for the A blocks in the range of about 2,000 to about 100,000 and for the B-blocks in the range of about 25,000 to 200,000.

In the styrene-olefin-styrene rubbers the content of styrene units will normally be 40% by weight or below. Such block copolymer will be an elastomer having two glass transition temperatures, one being below room temperature and the other considerably above room temperature. The aliphatic blocks may for instance be based on isoprene or butadiene. Very suitable examples of such block copolymers are "Cariflex" ® Tr-1107 and "Kraton" ® 101, both supplied by Shell Chemical Co. The aliphatic blocks may also be of polyisobutylene or based on some other short chain alkadiene or alkamonoene such as mixtures of ethylene and butylene.

In contrast the styrene-isobutylene copolymer employed according to U.S. Pat. No. 3,908,658, discussed herein above, is a random styrene-isobutylene copolymer having a much higher content of sytrene units (about 90%) than of isobutylene units. That product is a tackifier resin having a melting point around 90° C.

According to the invention it is especially preferred to use as the physically cross-linked elastomer a styrene-isoprene-styrene block copolymer. The above mentioned "Cariflex" Tr 1107 is a styrene-isoprene-styrene block copolymer whereas "Kraton" 101 is a styrene-butadiene-styrene elastomer (block copolymer) requiring no vulcanisation.

Other preferred elastomers to use according to the invention are ethylene-propylene block copolymers. They are also A-B-A block copolymers where the end blocks may be either polyethylene or polypropylene while the elastomeric midblock is a random copolymer of ethylene-propylene. These elastomers are called EPR rubbers. Examples of elastomers of this type are various materials supplied by E. I. du Pont de Nemours & Company under the common trade mark "Nordel".

In contradistinction to the abovementioned elastomers, it is generally found that the ethylene-vinylacetate copolymers (EVA polymers) although having some crystallinity do not have sufficient degree of "physical crosslinks" to be useful in the present invention.

Seals made of hydrocolloids and EVA polymers are found to be unelastic and loose integrity on swelling in water.

As already mentioned the gel-like composition will preferably according to the invention contain one or more hydrocarbon tackifier resins homogenously distributed in and forming part of the continuous phase of the composition. This tackifier increases the adhesive properties of the composition and is preferably a terpene tackifier resin or a dicyclopentadiene based tackifier resin. Especially preferred according to the invention as hydrocarbon tackifier resin component are polymers and copolymers of dicyclopentadiene, alpha-pinene and beta-pinene.

Moreover, according to the invention, there will preferably be an oil extender present in the gel-like composition. The oil extender will lower the elastic modulus of the material, being compatible with the soft elastic part of the elastomer. We have however found that the choice of oil may be a critical factor, especially as the cross-links in the cross-linked elastomer are of the physical type described above. With the styrene-olefin-styrene block copolymers we have found that according to the invention oils selected from the group consisting of paraffin oil, polybutene oils, vegetable oils and mixtures thereof may be used. Oils of a more polar nature tend to decrease the elastic properties, particularly increasing the permanent set. One possible explanation of this could be that the polar oils are too compatible with the styrene blocks of the polymer chains and thereby their ability to function as cross-links is reduced.

Further components may be present as long as they do not influence the properties desired and explained in undesired direction. In most cases it will be desirable to have an antioxidant present in the composition but actually, antioxidants are present in many commercial rubbers. Further components such as medicaments, disinfectants, bactericides and the like may be present but do not form part of the present invention.

The relative amounts of the three components will be discussed later but it should be mentioned here that the kinds and amounts of the components must be such that they form an adhesive gel having a low modulus of elasticity, low set and high elongation at break and a melting point above 40° C.; in this connection, the melting point is the temperature at which crystalline or glass-like segments or part of the elastomer melt in the gel.

An important effect of the "hard" block, functioning as cross links, is that the material and shaped objects made thereof in admixture with the hydrocolloid will retain their integrity during swelling of the hydrocolloid in water whereby such object can be removed from the skin of the patient after use and will not flow. In contradistinction hereto, the styrene-isobutylene copolymer used according to U.S. Pat. No. 3,908,658 will behave as a viscous liquid and flow, and the seal will lose its integrity on swelling in water.

The purpose of incorporating the hydrocolloid in the other components so as to form the gel-like composition is to retain a tight seal both between the shaped sealing material and the stoma, and between the sealing material and the skin (epidermis), even in cases where they release large amounts of liquid and moisture in the form of intestinal juice and sweat.

Conventional adhesive bandages such as plasters loose the grip and adhesiveness when exposed to moisture and in use for ostomy devices this will frequently result in damages such as cauterization of the skin of the patient. The hydrocolloids used according to the present invention swell when exposed to water and after some time, for instance after ½ to 4 hours take over the adhesive effect. A permanent adhesive effect of the present sealing material is obtained when there is equilibrium between the amount of water released from skin and stoma, and the amount of water penetrating into the sealing disc or plate.

An important property of a hydrocolloid to be suitable for use in the sealing material according to the invention is that it is able to swell rapidly and to transport water rapidly. It has been found that starch is a hydrocolloid not very suitable for the present purpose. The hydrocolloid must be water-swellable.

Examples of suitable hydrocolloids are carboxymethyl starches or carboxy methyl celluloses and alkali metal derivatives thereof, polyvinylalcohol, gelatin, powdered pectin, natural gums such as gum guar, gum arabic, locust bean gum, karaya and the like, high molecular weight carbowax, carboxypolymethylene and the like.

The most preferred hydrocolloids according to the invention are sodium carboxymethyl cellulose and guar gum and especially mixtures thereof. According to the invention it has been found that the best mixture of hydrocolloids for use in the sealing material according to the invention is a mixture of approximately 36 parts by weight of sodium carboxymethyl cellulose to 16 parts by weight of guar gum.

The type of antioxidant is not very critical and anybody skilled in the art can find usable examples in ordinary reference books. Examples are butylated hydroxytoluenes such as methylene-bis-(4-methyl-6-t-butylophenol) or 1-hydroxy-2,6-di-t-butyl-4-methylbenzene. In some cases the antioxidant is superfluous, and even when present, it is not always necessary to incorporate it into the material when making it because some commercial elastomers (including some of those usable in the present invention) do contain an antioxidant.

It is essential for a sealing material according to the invention and specifically for a seal made thereof that the components are chosen in a manner so that the other components retain even in admixture with the desired amount of hydrocolloid a low modulus of elasticity, a large elongation and a low set. For comparison, it has been found by experiment that a combination of vinyl polymer, tackifier and mineral oil according to Example III in U.S. Pat. No. 3,908,658 (that Example prescribes 100 g of an ethylene-vinyl acetate copolymer containing 17.5–18.5% vinyl acetate unit per 200 g heavy mineral oil, 300 g styrene-isobutylene random copolymer containing 90% styrene units and 200 g pregelatinized starch as hydrocolloid), but without filler (hydrocolloid) has a relatively large elongation at break and, in view of the present purpose, a too high modulus of elasticity and too high set. By the addition of filler (hydrocolloid) to bring the mass into accordance with Example III of the specification quoted, the elongation at break decreases dramatically and modulus of elasticity and set are increased drastically so that the material is unsuitable for the purpose aimed at with the present invention.

The amounts of the components may vary within wide limits. Disregarding the antioxidant the amount of which will be comparatively small and not normally exceeding 2% by weight, the amount of hydrocolloid or mixture of hydrocolloids may vary according to the invention from about 20% to about 80%, calculated on the weight of the entire amount of the gel-like composition. A preferred range of the hydrocolloid or mixture of hydrocolloids is 40–65% by weight, still more preferred 48–57% by weight and especially 50–55%, for example about 52% by weight of the entire mass.

The relative amounts of the other components to some degree depend upon the amount of hydrocolloid because as this influences the adhesive properties as described and also influence the softness and other properties. However, assuming 50% by weight of hydrocolloid or mixture of hydrocolloids as standard, the amount of physically cross-linked elastomer according to the invention will normally vary within the limits 2–40% by weight of the entire gel-like composition; especially the amount of the physically cross-linked elastomer will be 4–15% and most preferred about 9–10% by weight. The amount of tackifier resin according to the invention will usually be somewhat higher, usually of the order 5–50% by weight, more preferred 10–30%, still more preferred 15–25% and most preferred about 19–20% by weight. The amount of oil extender will be of approximately same order of magnitude as the two last mentioned components. It may be 0–50% by weight, especially 15–25% and most preferably 19–20% by weight.

In a preferred embodiment of the invention, this gel-like composition contains 40–65% by weight of the hydrocolloid, 5–50% by weight of the hydrocarbon resin tackifier and 2–40% by weight of the physically cross-linked elastomer. In a more preferred composition the gel-like composition contains 48–57% by weight of the hydrocolloid, 9–10% by weight of the physically cross-linked elastomer, about 17–20% by weight of the hydrocarbon tackifier resin and 15–25% by weight of the extender oil.

The most preferred composition according to the invention is one wherein the gel-like composition is composed of 9–10% by weight of styrene-isoprene block copolymer as the physically cross-linked elastomer, 17–20% by weight of fully hydrogenated polydicyclopentadiene tackifier resin, 17–20% by weight of liquid paraffin (paraffin oil) as oil extender, 33–39% by weight of sodium carboxymethyl cellulose as one and 15–17% by weight of guar gum as the other hydrocolloid.

The material will normally be molded into circular or polygonal discs or plates, especially rectangular or preferably approximately square plates with rounded corners, or into rings, in either case normally with a central opening of a suitable diameter so as to fit around the protruding stoma, the molded sealing material to be used in connection with stoma pouches or other stoma devices. As such physical structure is not in itself part of the present invention, it will not be described further. However, it is partly shown on the drawing accompanying the present specification, and the position of adhesive rings as mentioned can also be seen in the U.S. Pat. No. 3,908,658, especially FIG. 4, which is hereby for this limited purpose made part of the present specification. The rings, discs or plates may be sold as such, possibly supplied with removable release liners; or they may form part of some stoma device as those mentioned, or other ostomy systems.

The shaped sealing material may be prepared in the following manner: The physically cross-linked elastomer is heated at a suitable temperature; normally this will be in the range of 80°–170° C. but depends of course of the precise nature thereof; if the composition shall contain a hydrocarbon resin tackifier and an oil extender as described, these are normally admixed with the elastomer before the heating. When the desired temperature is reached and the mixture of the elastomer, the tackifier and possibly the oil extender is homogeneous, the hydrocolloid or a mixture of desired hydrocolloids is added at the same temperature and stirring is carried out until the blend is substantially even.

Then the mass is cooled and later reheated and molded into desired shape or sheets of desired thickness, or it is directly molded into rings, discs or sheets of desired thickness, from which the ultimate rings, discs or plates can be cut or punched.

EXAMPLES CL EXAMPLE 1

In this example the properties of a number of sealing materials are compared. Sealing materials A through F are sealing materials according to the present invention. Materials G, H, and I are prepared in accordance with the disclosure in U.S. Pat. No. 3,980,658, and finally material K is in accordance with U.S. Pat. No. 3,339,546 and sold commercially under the trade name "Stomahesive".

The results of the tests are shown in Table I. The exact composition of the individual samples is shown in Table III, placed after Example 2 and in an appendix to this the materials mentioned by trade names are identified.

The individual compositions were prepared as follows.

Material A (according to the invention)
100 g of "Nordel" 2522 (an ethylene-propylene-ethylene block copolymer of rather low crystallinity) and 100 g of "Nordel" 2722 (an ethylene-propylene-ethylene block copolymer of higher crystallinity) were mixed at 90° C. with 200 of liquid paraffin (Pharmacopea Nordica) and 400 g of "Arcon" P90 (a hydrogenated polycyclopentadiene tackifier resin). When the mixture had become homogeneous 800 g of guar gum were added, and the composition was mixed until a homogeneous dispersion was obtained.

Material B (according to the invention)
83 g og "Cariflex" TR 1107 (a styrene-isoprene-styrene block copolymer containing about 28% styrene) were mixed at 130° C. with 166 g of "Arcon" P90 and 250 g of liquid paraffin. When the mixture became homogeneous 500 g of hydrocolloid with a mixture of ⅔ guar gum and ⅓ "Polyox Coagulant" (polyethylene oxide) were admixed.

Materials C, D and F (according to the invention) were likewise based on "Cariflex" TR 1107 as the physically cross-linked elastomer and were made in the same manner as material B: the elastomer and other components exept the hydrocolloid were mixed at 130° C. and when homogeneous admixed with the hydrocolloid.

Material E (according to the invention) was also made as material B and the main difference is that "Cariflex" is replaced by "Kraton" G 1652 which is a polystyrene-polyolefin-polystyrene block copolymer.

Material G (representing prior art)
200 g of liquid paraffin were heated at 163° C. and 100 g of "Elvax" 250 (an ethylene-vinylacetate copolymer containing about 27.2–28.8% vinyl acetate units) were mixed while stirring until the "Elvax" had become dissolved. Thereafter 300 g of "Klyrvel" (a random copolymer of styrene and isobutylene containing 90% styrene and 10% isobutylene units) were added under stirring until dissolved.

Material H (representing prior art)
100 g of the mixture obtained as Material G were admixed at 110° C. with 100 g of guar gum.

Material I (representing prior art)
100 g of "Elvax" 420 (an ethylene-vinylacetate copolymer containing about 17.5–18.5% vinyl acetate units) were heated at 150° C. together with 200 g of liquid paraffin while stirring. 300 g of "Klyrvel" 900 were added to the homogeneous mixture. When this was dissolved the mixture was cooled at 100° C. and 600 g of guar gum admixed until the entire mass was homogeneous.

Material K (representing prior art)
A commercial product, "Stomahesive" from Squibb Hospital Division, E. R. Squibb & Sons, Inc., New York, N.Y. 10022; the commercial product has adhesively bonded thereto on one side a polyethylene film; this was removed in order to be able to measure the elasticity properties of the product.

According to the declaration concerning this material it consists of a polyisobutylene matrix into which is admixed a hydrocolloid mixture consisting of gelatin, pectin, and sodium carboxymethyl cellulose. This is in accordance with Example 1 in the aforementioned U.S. Pat. No. 3,339,546 to Chen.

The mechanical properties of these ten materials were tested by clamping a sample (size between clamps: 90 mm long, 5 mm wide, 3 mm thick) between two clamps in an Instron tester (ASTM D 638-64 T). A recording was made of force versus elongation at a given speed of elongation.

After maximum elongation the sample was relaxed at the same speed and the permanent set was measured.

Two cycles were made for each material. The first cycle (I) was performed on the sample not previously stretched. The second cycle (II) was performed on the sample stretched and relaxed in cycle I. The results are given in table I. The first column of figures shows the speed at which the elongation was carried out, and the third column the force necessary to carry out the elongation at that speed. The second column shows the maximum elongation to which each cycle was carried out.

The last column in the Table shows the set remaining after relaxation; relaxation occurs when the force necessary to cause the elongation is removed. The permanent set is expressed in per cent of the elongation used in the individual cycle.

TABLE I

| Material | | Elongation speed, cm/min. | Maximum elongation % | Maximum force, grams | Maximum force (grams) pr. max elongation | Permanent set % |
|---|---|---|---|---|---|---|
| A | I | 6 | 30 | 12.6 | 42 | 10 |
|   | II | 6 | 53 | 12.9 | 24 | 11 |
| B | I | 6 | 20 | 6.9 | 35 | 10 |

TABLE I-continued

| Material | | Elongation speed, cm/min. | Maximum elongation % | Maximum force, grams | Maximum force (grams) pr. max elongation | Permanent set % |
|---|---|---|---|---|---|---|
| | II | 6 | 48 | 12.6 | 26 | 8 |
| C | I | 6 | 50 | 64 | 128 | 28 |
| | II | 6 | 100 | 51 | 51 | 24 |
| D | I | 6 | 50 | 22 | 44 | 0 |
| | II | 6 | 100 | 37 | 37 | 0 |
| E | I | 6 | 50 | 26 | 52 | 26 |
| | II | 6 | 100 | 36 | 36 | 24 |
| F | I | 6 | 50 | 78 | 156 | 28 |
| | II | 6 | 100 | 98 | 98 | 27 |
| G | I | 6 | 28 | 9.8 | 37 | 35 |
| | II | 6 | 100 | 13.3 | 13 | 42 |
| H | I | 6 | 23 | 13.1 | 57 | 66 |
| I | I | 6 | 12 | 11 | 92 | 79 |
| | II | 6 | Break at 25 | 11 | — | — |
| K | I | ;12 | 0,4 0,7 | 74 | 9600 | 31 |
| | II | | 0,4 0,97 | 80 | 8300 | 28 |
| | III | | ,4 1,03(break) | 70 | — | — |

From the table it will be seen that the materials according to the invention (A through F) all have a low permanent set combined with an ability to give large elongation at low force. It is also seen that repeated elongation does not increase the permanent set.

In contrast the known materials H, I, and K have a high permanent set, and this increases with repeated elongation. The high permanent set illustrates well the manual kneadability found desirable by Marsan which however makes the material unsuitable for the present purpose.

Material G does not contain a hydrocolloid and it is seen that in this form the force at maximum elongation is relatively small.

When however a hydrocolloid is added to give material H the material becomes very stiff.

Material K has extremely poor properties. When elongated at the same speed as the other samples it breaks well before 1% elongation. The figures in the table are obtained at the very low speed of 0.4 cm/min and yet the material breaks at about 1% elongation. The stiffness of the material is illustrated by the high force required and the permanent set illustrates the viscous liquid nature of the composition.

From the materials in table I seals were made in the form of ring-shaped discs with a thickness of about 3 mm. These shaped seals were used by stoma patients in conjunction with conventional stoma bags.

The seals made from materials A, B, D, D, E, and F maintained perfect sealing both between the stoma bag and the skin and between the stoma and the skin, and after the test the patients did not show any sign of skin irritation.

With materials H, I, and K leakage from the interior of the stoma bag to the skin occurred, and skin irritation was observed. It was also found especially with material K that when the intestine liquid swelled the hydrocolloid the shaped seal lost its integrity and flowed away and was vary difficult to remove from the skin after use. This was in marked contrast to the seals according to the invention.

EXAMPLE 2

Further samples were prepared in accordance with the invention with a standard content of 50% of hydrocolloid in order to demonstrate variations in composition of the rubber phase. The materials were tested in the same manner as described in Example 1 and the results are shown in Table II. In this is for comparison also incorporated the results of the testing of material I as shown in Table I (i.e. Marsan sample containing 50% guar gum).

TABLE II

| Material | | Elongation speed, cm/min. | Maximum elongation % | Maximum force, grams | Maximum force (grams) per. max elongation | Permanent set % |
|---|---|---|---|---|---|---|
| L | I | 6 | 32 | 2.9 | 9.1 | 12 |
| | II | 6 | 173 | 4.6 | 2.7 | 7.4 |
| M | I | 6 | 50 | 32 | 64 | 7 |
| | II | 6 | 100 | 37 | 37 | 7 |
| N | I | 6 | 50 | 27 | 54 | 11 |
| | II | 6 | 100 | 30 | 30 | 7 |
| O | I | 6 | 50 | 24 | 48 | 20 |
| | II | 6 | 100 | 30 | 30 | 16 |
| P | I | 6 | 50 | 94 | 188 | 28 |
| | II | 6 | 100 | 122 | 122 | 26 |
| I | I | 6 | 12 | 11 | 92 | 79 |
| | II | 6 | Break at 25 | 11 | — | — |

TABLE III

| | Materials tested in Examples 1 and 2 | |
|---|---|---|
| A | "Nordel"2522[1] | 6.3% |
| | "Nordel"2722[2] | 6.3% |
| | "Arcon"p 90[3] | 12.5% |
| | Liquid paraffin[4] | 25.0% |
| | Guar gum[5] | 50.0% |
| B | "Cariflex" TR 1107[6] | 9.2% |
| | "Arcon" p 90 | 18.3% |
| | Liquid paraffin | 27.5% |
| | Guar gum | 30.0% |
| | "Polyox" coagulant[7] | 15.0% |
| C | "Cariflex" TR 1107 | 7.0% |
| | "Arcon" p 90 | 14.0% |
| | Liquid paraffin | 14.0% |
| | "Versicol" (sodiumpolyacrylat)[8] | 45.0% |
| | CMC[9] | 20.0% |
| D | "Cariflex" TR 1107 | 15.0% |
| | "Arcon" p 90 | 30.0% |
| | Liquid paraffin | 30.0% |
| | Guar gum | 20.0% |
| | "Hercofloc" (polyacrylamide[10]) | 5.0% |
| E | "Kraton" G 1652[11] | 4.4% |
| | "Arcon" p 90 | 32.8% |
| | Liquid paraffin | 32.8% |
| | CMC | 30.0% |
| F | "Cariflex" TR 107 | 18.9% |
| | "Arcon" p 90 | 37.8% |
| | "Staybelite" ester[12] | 13.2% |
| | "Versicol" | 30.0% |
| G | "Elvax" 250[13] | 16.7% |
| | "Klyrvel" 900[14] | 50.0% |
| | Liquid paraffin | 33.3% |
| H | "Elvax" 250 | 8.3% |
| | "Klyrvel" 900 | 25.0% |
| | Liquid paraffin | 16.7% |
| | Guar gum | 50.0% |
| I | "Elvax;38 420[15] | 8.3% |
| | "Klyrvel" 900 | 25.0% |
| | Liquid paraffin | 16.7% |
| | Guar gum | 50.0% |
| K | Polyisobutylene | app. 42.0% |
| | Pectin, gelatin, CMC (assumed from patent and literature; "Stomahesive") | — 58.0% |
| L | "Cariflex" TR 1107 | 8.3% |
| | "Arcon" p 90 | 16.7% |
| | Liquid paraffin | 25.0% |
| | Guar gum | 50.0% |
| M | "Cariflex" TR 1107 | 10.0% |
| | "Arcon" p 90 | 20.0% |
| | Liquid paraffin | 20.0% |
| | Pectin[16] | 25.0% |
| | Xanthan gum ("Rhodopol")[17] | 25.0% |
| N | "Cariflex" TR 1107 | 11.1% |

TABLE III-continued

| Materials tested in Examples 1 and 2 | | |
|---|---|---|
| | "Arcon" p 90 | 22.2% |
| | Liquid paraffin | 11.1% |
| | Groundnut oil | 5.6% |
| | Karaya gum[8,19)] | 50.0% |
| O | "Cariflex" TR 1107 | 10.6% |
| | "Arcon" p 90 | 21.2% |
| | Polyisobutylene ("Oronite"16[(20)]) | 18.1% |
| | Guar gum | 50.0% |
| P | "Cariflex" TR 1107 | 13.0% |
| | "Arcon" p 90 | 26.0% |
| | "Hercolyn;38 D[(21)]" | 1.3% |
| | Liquid paraffin | 9.7% |
| | Guar gum | 50.0% |

Notes to Table III
[(1)]Ethylene-Propylene block copolymer manufactured by E.I. du Pont de Nemours & Co.
[(2)]Ethylene-Propylene block copolymer manufactured by E.I. du Pont de Nemours & Co.
[(3)]Hydrogenated poly cyclopentadien tackifier manufactured by ARAKAWA Forest Chemical Industries Ltd.
[(4)]Paraffin oil: "Risella" 33 from Shell Chemical Co.
[(5)]Guar Gum: a natural plant gum from CisAlpina/Italy.
[(6)]A styrene-isoprene-styrene blockcopolymer from Shell Chemical Co.
[(7)]A polyethyleneoxide from Union Carbide Corporation.
[(8)]The sodium polyacrylate is marketed by Allied Colloids.
[(9)]Carboxymethylcellulose from Hoechst-Germany "Tylose" CB 30.000.
[(10)]A polyacrylamide hydrocolloid manufactured by Hercules, Inc.
[(11)]"Kraton" G1652 is a polystyrene-polyolefin-polystyrene blockcopolymer from Shell Chemical Co.
[(12)]"Staybelite" ester E3 is the glycerolester of wood resin manufactured by Hercules, Inc.
[(13)]"Elvax" 250 is a ethylene-vinylacetate copolymer marketed by E.I. du Pont de Nemours & Co.
[(14)] "Klyrvel" 900 is a styrene-isobutylene copolymer marketed by Velsiocol Chemical Corporation.
[(15)]"Elvax;38 420 is a ethylene-vinylacetate copolymer marketed by E.I. du Pont de Nemours & Co.
[(16)]A natural gum from A/S Kobenhavns Pektinfabrik.
[(17)]A natural gum solid by Rhone-Poulenc.
[(18)]Groundnut oil is pharmaceutic grade.
[(19)]Karaya gum
[(20)]"Oronite" 16 is manufactured by Chevron Chemical Co.
[(21)]"Hercolyn" D is the glycerol ester of selected stabilized resin acids manufactured by Hercules, Inc.

EXAMPLE 3

Four samples of the sealing materials in accordance with the invention described in this patent have been compared to "Stomahesive" ("Stomahesive" is a commercially available product, a dispersion of a hydrocolloid blend comprising gelatin, sodium carboxymethyl cellulose, and pectin in polyisobutylene, cf. U.S. Pat. No. 3,339,546), when tested on a person who has had the surgical operation called ileostomy. The faecal material excreted from an ileostomy is almost liquid and has a high content of enzymens which are aggressive to the human skin.

The test period was two days. The patient showed irritation of the skin just around the stoma when using the "Stomahesive". Further the seal was difficult to remove, being dissolved from the edge and losing integrity. When using the sealing materials according to this patent no irritation could be observed after the test period, and the seal was easily removed as a whole although quite some swelling had taken place under the very humid conditions.

Table IV shows schematically the four compositions tested.

TABLE IV

| Sample No. | Q | R | S | T |
|---|---|---|---|---|
| Styrene-isoprene-styrene block copolymer (1) | 9.6 | 10.0 | 8.3 | |
| Styrene-butadiene-styrene block copolymer (2) | | | | 12.5 |
| alpha beta pinene tackifier resin | | 20.6 | | |
| Fully hydrogenated poly-dicyclopentadiene tackifier resin | 19.2 | | | |
| Hydrocarbon tackifier resin (3) | | | 16.7 | |
| beta pinene based tackifier resin | | | | 20 |
| Liquid paraffin | 19.2 | 18 | 25 | |
| Groundnut oil | | | | 22 |
| Sodium carboxymethyl cellulose | 36.4 | 32 | 30 | 27 |
| Pectin | | 20 | | |
| Guar gum | 15.6 | | 8 | 18.5 |
| Hydroxypropyl cellulose | | | 12 | |

"Cariflex" TR 1107
(2)"Solprene" 411, a styrene-butadiene block copolymer sold by Phillips Petroleum Co.
(3)"Betaprene" H-100, a hydrocarbon resin derived from monomeric olefins and diolefins, marketed by Reichold Chemicals Inc; iodine-number 100.

Since the percentage of the individual ingredients in the Stomahesive is not exactly known, a similar product was prepared using the information in example 1 of U.S. Pat. No. 3,339,546. This material was also tested and gave exactly the same results as the commercial material.

What we claim is:

1. In an ostomy system for covering intestinal and similar stomas in a human body, comprising an ostomy device surrounding or covering said stoma and attached to the human body by sealing means, the improvement which comprises utilizing as a sealing means a shaped, gel-like composition comprising at least one physically cross-linked elastomer selected from the group consisting of styrene-olefin-styrene block copolymers and ethylene-propylene block copolymers, forming a continuous phase and at least one hydrocolloid dispersed therein, said hydrocolloid being selected from the group consisting of guar gum, pectin, sodium carboxymethyl cellulose, sodium polyacrylate, and mixtures thereof, said compositions also containing a hydrocarbon tackifier selected from the group consisting of polymers and copolymers of dicylopentadiene, alpha-pinene or beta-pinene, and wherein said gel-like composition has a low resistance to quick deformation and a rapid recovery to its original shape after deformation, whereby the seal between the ostomy device and epidermis of the human body as well as the seal between the stoma and the portion of epidermis exposable to discharge from the stoma are maintained intact, even under rapid body movement.

2. An ostomy system as claimed in claim 1, wherein the styrene-olefine-styrene block copolymer is a styrene-isopropene-styrene block copolymer.

3. An ostomy system as claimed in claim 1, wherein the physically cross-linked elastomer is an ethylene-propylene block copolymer.

4. An ostomy system as claimed in claim 1, wherein at least part of the hydrocolloid is sodium carboxymethyl cellulose.

5. An ostomy system as claimed in claim 1, wherein at least part of the hydrocolloid is guar gum.

6. An ostomy system as claimed in claim 1, wherein the gel-like composition further contains at least one oil extender which forms part of the continuous phase.

7. An ostomy system as claimed in claim 6, wherein the oil extender is selected from the class consisting of paraffin oils, polybutene and vegetable oils.

8. An ostomy system as claimed in claim 6, wherein the gel-like composition contains about 48-57% by weight of the hydrocolloid, about 9-10% by weight of the physically cross-linked elastomer, about 17-20% by weight of the hydrocarbon tackifier resin and about 15–25% by weight of the extender oil.

9. An ostomy system as claimed in claim 6, wherein the gel-like composition is composed of 9–10% by weight of styrene-isoprene-styrene block copolymer as the physically cross-linked elastomer, 17–20% by weight of fully hydrogenated poly-dicyclopentadiene tackifier resin, 17–20% by weight of liquid paraffin as oil extender, 33–39% by weight of sodium carboxymethyl cellulose as one and 15–17% by weight of guar gum as the other hydrocolloid.

10. An ostomy system as claimed in claim 1, wherein the gel-like composition further contains an antioxidant.

11. An ostomy system as claimed in claim 10, wherein the antioxidant is selected from the class consisting of butylated hydroxytoluenes.

12. An ostomy system as claimed in claim 10, wherein the amount of antioxidant in the gel-like composition does not exceed 2% by weight.

13. An ostomy system as claimed in claim 1, wherein the gel-like composition contains from about 20 to 80% by weight of the hydrocolloid, about 5–50% by weight of the hydrocarbon resin tackifier and about 2–40% by weight of the physically cross-linked elastomer.

14. An ostomy system as claimed in claim 13, wherein the gel-like composition contains about 40–65% by weight of the hydrocolloid, about 15–35% by weight of the hydrocarbon tackifier resin and 4–15% by weight of the physically cross-linked elastomer.

15. An ostomy system as claimed in claim 1, wherein the shaped gel-like composition is shaped as a polygonal to circular disc with a substantially circular opening substantially fitting the outer perimeter of a protruding stoma in a patient's body.

16. In an ostomy system for covering intestinal and similar stomas in a human body, comprising an ostomy device surrounding or covering said stoma and attached to the human body by sealing means, the improvement which comprises utilizing as a sealing means a shaped, gel-like composition comprising at least one physically cross-linked elastomer selected from the group consisting of styrene-olefin-styrene block copolymers and ethylene-propylene block copolymers, forming a continuous phase and at least one hydrocolloid dispersed therein, said hydrocolloid being selected from the group consisting of guar gum, pectin, sodium carboxymethyl cellulose, sodium polyacrylate, and mixtures thereof, said compositions also containing a terpene resin tackifier, and wherein said gel-like composition has a low resistance to quick deformation and a rapid recovery to its original shape after deformation, whereby the seal between the ostomy device and epidermis of the human body as well as the seal between the stoma and the portion of epidermis exposable to discharge from the stoma are maintained intact, even under rapid body movement.

17. An ostomy system as claimed in claim 16, wherein the gel-like composition also contains an oil extender selected from the class consisting of paraffin oil, polybutene and vegetable oils.

18. An ostomy system as claimed in claim 12, wherein the oil extender is present in amount ranging in amount from 10–30% by weight.

19. An ostomy system as claimed in claim 17, wherein the gel-like composition contains from 48–57% by weight of the hydrocolloid, about 9–10% by weight of the physically cross-linked elastomer, about 17–20% of hydrocarbon resin tackifier and about 19–20% by weight of the oil extender.

20. An ostomy system as claimed in claim 16, wherein at least part of hydrocolloid is guar gum.

21. An ostomy system as claimed in claim 16, wherein at least part of the hydrocolloid is sodium carboxymethyl cellulose.

22. An ostomy system as claimed in claim 16, wherein the gel-like composition contains from about 2 to 40% by weight of the physically cross-linked block copolymer, about 5–50% by weight of a terpene resin tackifier and about 20–80% by weight of the hydrocolloid.

* * * * *